US009655699B2

(12) United States Patent
Chen et al.

(10) Patent No.: US 9,655,699 B2
(45) Date of Patent: May 23, 2017

(54) ARTIFICIAL TEETHRIDGE AND FANG

(71) Applicants: Lieh-Tang Chen, Taichung (TW); Chen-Chu Chen, Taichung (TW)

(72) Inventors: Lieh-Tang Chen, Taichung (TW); Chen-Chu Chen, Taichung (TW)

(*) Notice: Subject to any disclaimer, the term of this patent is extended or adjusted under 35 U.S.C. 154(b) by 91 days.

(21) Appl. No.: 13/759,914

(22) Filed: Feb. 5, 2013

(65) Prior Publication Data
US 2013/0149668 A1 Jun. 13, 2013

Related U.S. Application Data

(63) Continuation-in-part of application No. 12/524,361, filed on Jul. 23, 2009, now abandoned.

(51) Int. Cl.
*A61C 8/00* (2006.01)
*A61C 13/01* (2006.01)
*A61C 13/097* (2006.01)

(52) U.S. Cl.
CPC .......... *A61C 13/01* (2013.01); *A61C 8/0022* (2013.01); *A61C 8/0031* (2013.01); *A61C 8/0068* (2013.01); *A61C 8/0075* (2013.01); *A61C 13/097* (2013.01)

(58) Field of Classification Search
CPC ..... A61C 13/01; A61C 13/097; A61C 8/0031; A61C 8/0068; A61C 8/0075
USPC .................................................. 433/172–174
See application file for complete search history.

(56) References Cited

U.S. PATENT DOCUMENTS

| 4,182,034 | A | * | 1/1980 | McCauley | 433/174 |
| 4,204,321 | A | * | 5/1980 | Scott | A61C 13/2656 |
| | | | | | 433/177 |
| 4,571,185 | A | * | 2/1986 | Rota | 433/173 |
| 4,808,110 | A | * | 2/1989 | Rametti | 433/172 |
| 4,828,492 | A | * | 5/1989 | Agnone | 433/173 |
| 4,904,186 | A | * | 2/1990 | Mays | 433/172 |
| 5,133,662 | A | * | 7/1992 | Metcalfe | 433/169 |
| 5,201,736 | A | * | 4/1993 | Strauss | 606/285 |
| 5,906,489 | A | * | 5/1999 | Khazzam et al. | 433/176 |
| 5,944,526 | A | * | 8/1999 | Liu | 433/176 |
| 5,976,140 | A | * | 11/1999 | Haas | 606/328 |
| 6,287,118 | B1 | * | 9/2001 | Naganuma et al. | 433/176 |
| 6,540,515 | B1 | * | 4/2003 | Tanaka | A61C 8/0081 |
| | | | | | 433/189 |

(Continued)

*Primary Examiner* — Cris L Rodriguez
*Assistant Examiner* — Mirayda A Aponte
(74) *Attorney, Agent, or Firm* — Chun-Ming Shih

(57) ABSTRACT

An artificial teethridge has an arched top and an arched bottom. The top and the bottom of the artificial teethridge are curved toward the same direction. The thickness of the artificial teethridge is relatively thicker at central part and gradually becomes thinner toward two lateral sides. A fang is formed integrally on the top of the artificial teethridge. The artificial teethridge, the fang and a prosthesis are an integral structure, whereby the artificial teethridge, the fang and the prosthesis form a mechanical conduction structure. The bottom surface of the artificial teethridge has a complementary structure which can be tightly matched and fixed on each point of the top surface of the alveolar bone without any gap. A dental neck is formed integrally between the artificial teethridge and prosthesis, which is formed in a waisted shape that is narrower at middle section and gradually becomes wider toward to two terminal sections.

4 Claims, 8 Drawing Sheets

(56) References Cited

U.S. PATENT DOCUMENTS 8,100,691 B2 * 1/2012 Sprenger .................. 433/172
8,562,345 B2 * 10/2013 Bluemli et al. ............. 433/172

* cited by examiner

ARTIFICIAL TEETHRIDGE AND FANG

CROSS-REFERENCE

This application is a continuation-in-part (CIP) application of U.S. patent application Ser. No. 12/524,361, filed on Jul. 23, 2009.

FIELD OF THE INVENTION

The present invention relates to a structure of dental fixture, particularly relates to an integral structure of the artificial teethridge, the fang and the prosthesis which are fixed on the cortical bone of the alveolar bone. The artificial teethridge and fang can well spread and transmit the chewing force to the alveolar bone uniformly, and load the chewing force by entire top surface of the alveolar bone.

DESCRIPTION OF THE RELATED ART

In present days, there are many different methods to mount the denture. The earliest method is to directly mount the denture on the gingival. This method is quite simple, however, the patient usually have an uncomfortable feeling of having foreign body in the mouth, and can not chew the hard food. Other disadvantages include difficult to fix the denture on the jaw, and always causing gingivitis, and so on.

Another method is to implant a fixture in the jaw, which is so called "dental implant" and is common nowadays. Many former patents have disclosed this method, such as U.S. Pat. Nos. 4,359,318, 6,322,364, 5,542,847, 6,916,177, 5,306,149, 6,991,463, 3,925,892, 4,722,687, 4,344,757, 4,964,801 and 6,655,962. The fundamental issue of these designs is about the load of the chewing force on a single implant. Furthermore, the implant is anchored on the incompact cancellous alveolar bone which has less density and less hardness. Hence, the capacity of loading force is limited. Dental implant is impossible or will fail when the alveolar bone losses seriously, which results from the alveolar bone having insufficient height and width for the implant. Even if implanted, the twisting force and shear force during chewing will lead to implant loose or alveolar damage. In addition, there is a troublesome problem, i.e. it must wait about six months for the alveolar bone to osseointegrate with the implant, and accordingly the patient has to endure the long-term trouble chewing before installing the denture.

Besides, a part of implanted fixtures have a mounting structure, such as U type, saddle type, covering type, etc., and some other parts of implanted fixtures have an auxiliary structure, such as loop, plat, washer, shoulder, etc., these implanted fixtures have been disclosed in U.S. Pat. Nos. 5,906,489, 4,702,697, 5,052,930, 5,513,989, 3,579,829, 4,121,340, 4,379,694, 4,531,916, 5,201,736, 5,759,033, 5,944,526, 6,287,118, 6,991,463, 4,728,331, 4,321,914, 4,531,916, 4,253,833, 5,573,401, 6,250,923, 6,273,720, 4,073,999, 6,287,118, 5,769,637, US2006/0154205A1, FR1113889, RU2217097, BG51338, WO0239921, WO2008062256, RU2145819, and CN1537516 (200310101638.6). Although these implanted fixtures have the mounting or accessory designs which are different from the single implant, they all focus on the issue of anchoring, and they still load the main force on the implant. These two types of structures are not a mechanical conduction structure which is relatively thicker at central part and gradually becomes thinner toward two lateral sides, nor are a mechanical support structure which has a complementary structure to match and fix on the top surface of the cortical bone of alveolar bone. Therefore these structures can not spread and transmit the force uniformly, nor can load the force to the strong cortical bone surface of alveolar bone. Most of these patents still load the force on the implant, which anchors on the incompact cancellous alveolar bone, or on a few prominent points of the cortical bone, so that they have insufficient area to load the chewing force on the alveolar bone, nor can spread and transmit the force uniformly. It still has a disadvantage of easily damage. Furthermore, most of these structures are not integral designs, so that the structures are fragile, and the capacity of the force conduction is not good.

Other designs, such as DE202006011340U and WO0001318A1, disclose a common implant fixture which anchors on the alveolar bone. They are not mechanical conduction structures or mechanical support structures to spread and transmit the loading force uniformly and load the chewing force on the cortical bone of the alveolar bone.

In conclusion of the conventional patents mentioned above, most of the dental implants in the present market still focus on how to firmly anchor the implant. Because all the occlusal pressure, twisting force and shear force, which load on the prosthesis during chewing, can not be spread and transmit out, it is necessary to provide a better anchoring way and a strong structure to load the chewing force. The entire prior arts focus on how to firmly anchor the implant on the alveolar bone, but most of the designs anchor on the incompact cancellous alveolar bone rather than the strong cortical bone of the alveolar bone. These designs neglect that how to load the force with balance and uniformity, and neglect that it may causes the alveolar damage and alveolar atrophy of the residual alveolar ridge.

All the conventional patents mentioned above only focus on the structure of single prosthesis. There are other designs disclose the structure of full denture, such as U.S. Pat. Nos. 4,225,668, 4,741,698, 4,767,328, 5,098,296, 6,382,975, 6,685,473, 6,692,254 and 7,234,940, which include inserting several single implants into the alveolar bone, and then connect the implants together with a bar or bridge structure atop the gingival. The bar or the bridge forms a supporting structure to load the full denture. Although these inventions have the structures which can well spread and transmit the chewing force, but still load the chewing force by a few single implants. These designs still have the same disadvantage as the above-mentioned single implant, such as limited loading force due to anchor the implant on the incompact cancellous alveolar bone which has a low density and hardness, and they can not be implanted on the atrophic alveolar bone which has insufficient height and width. Even if implanted, the twisting force and shear force will cause the implant loose or alveolar damage. Again, it must wait about six months for the alveolar bone to osseointegrate with the implant.

Besides, U.S. Pat. No. 2,836,890 patent discloses a structure of full denture which is fixed on the surface of the alveolar bone, but the bottom of this structure lacks of a complementary structure which can be tightly matched and fixed on the top surface of the alveolar bone without any gap. It still loads the chewing force on a few prominent points of the surface on the alveolar bone, and it further leads to the alveolar damage or alveolar atrophy of the prominent points on alveolar bone and will causes the implants loose. Furthermore, the full denture is not an integral structure, and it still fixes all of the prosthesis with screws. That is, the structure is fragile, and the force conduction is discontinuous, so that the occlusal pressure, twisting force, and shear force will cause the screw loose. Most importantly, the dental structure does not have a tapered post and a crescentshaped carrier. That is, it is not a mechanical conduction structure which can spread and transmit the loading force uniformly, so that the force conduction is not uniformly and the capacity of force loading is poor.

The patent of U.S. Pat. No. 4,379,694 discloses an arch structure of dental fixture. Although this structure is mounted on the alveolar bone, but the main structure is a flat metal plate without tapered post on the plate, and the plate is not relatively thicker at central part and gradually becomes thinner toward two lateral sides. That is, it is not a mechanical conduction structure which can spread and transmit the loading force uniformly. Furthermore, it is not an integral structure; it needs screws to secure the bridge or the prosthesis into a post head which has a threaded hole. Although this structure strengthen the fixing function, it still can not well spread and transmit the chewing force, and it is also a fragile structure.

Most importantly, for all the conventional patents as described above, the bottom surface of the dental structure lacks a complementary structure which can be tightly matched and fixed on the top surface of the alveolar bone without any gap. All of the dental structures can not spread and transmit the chewing force to each point of the surface on the alveolar bone uniformly, and the structures still load the chewing force onto a few prominent points of the surface on the alveolar bone, thus they further lead to the alveolar damage or alveolar atrophy of the alveolar bone and will cause the implants loose. In conclusion, the structures of these conventional patents are not designed to be a mechanical conduction structure, which has the function of "raft foundation", due to the fact that it is difficult to get a precise model of the alveolar bone in the early time, and that it is also difficult to fabricate the dental product with a complementary structure, which can be tightly matched and fixed on the top surface of the alveolar bone without any gap. However, the relative techniques are mature nowadays, such as the 3D photography, computer-aided design (CAD), computer numerical control (CNC) manufacture, and injection molding. It is not difficult to make a precise product with a surface totally complementary to the surface of the alveolar bone. It is also not a problem to make a mechanical conduction structure which is mounted and fixed on the surface of the alveolar bone, thus the loading force transmitted from the prosthesis can spread and transmit through this integral structure to each point of the top surface of the alveolar bone completely and uniformly. Accordingly it will no longer be a problem to load the chewing force by the firm cortical bone of the alveolar bone.

In order to address these afore mentioned issues, the present applicants have filed a PCT patent application, serial no. PCT/CN2007/000353, titled "Denture Carrier Fixed on The Surface of The Alveolar Bone". However, in order to make this product perfect and actively pursue the excellent innovation, we file this application in addition.

SUMMARY OF THE INVENTION

The primary objective of the present invention is to design an integral structure of the artificial teethridge, the fang and the prosthesis, which has a great capacity of force loading, and can transmit the chewing force uniformly and stably. In order to achieve the objective, the present invention designs a structure having a artificial teethrige which has an arched top and an arched bottom. The top and the bottom are curved toward the same direction, and the thickness is relatively thicker at central part and gradually becomes thinner toward two lateral sides, and then on the top of the artificial teethridge form integral with the fangs and the prosthesis, whereby the chewing force, which transmitted from the prosthesis, will spread and transmit outward and downward through this structure to entire top surface of the alveolar bone. Thereby, the chewing force will be spread and transmitted from a narrow surface of prosthesis to a greater surface of the alveolar bone by a mechanical conduction structure.

Moreover, the bottom surface of the artificial teethridge designs a complementary structure which can be tightly matched and fixed on the top surface of the alveolar bone without any gap (i.e. designs the bottom of the artificial teethridge having the concave surfaces to match the convex surfaces of the alveolar bone, or having the convex surfaces to match the concave surfaces of the alveolar bone, the concave and convex are complementary to each other. That is to say, the bottom surface of the artificial teethridge having a complementary structure tightly matched the top surface of the alveolar bone). Through this complementary arrangement, the loading force which transmits from the prosthesis can be spread and transmitted to each point of the top surface on the strong cortical bone of the alveolar bone completely and uniformly. This structure has mechanical support function like so-called "raft foundation" of architecture, which loads the chewing force transmitted from the prosthesis by each point of the top surface on the alveolar bone uniformly. The present invention uses the "raft foundation" in substitution for the traditional "pile foundation", thus the structure of the present invention will load the force stably and uniformly. That is to say, this mechanical support structure can load the chewing force completely and uniformly.

Besides, to avoid the weak point exist at this dental structure, the present invention does not combine separated parts of the structure by screws. Thereby this structure has no connecting portion which may cause a discontinuous transmission of force and reduce the capacity of force conduction. The present invention designs an integral structure which comprises the main part of force conduction and force supporting, so that it forms a strong and stable structure with great force support, uniform force dispersion, firm fixation, and well force conduction.

The present invention has three main characters aforesaid, and none of these main characters can be found in any prior arts. Each of the independent claims shown below (such as claim 1, 8, 14, 20, 26, 28, and 30) of the present invention has at least one of these three main characters. The summarization of these three main characters is as follows:

1. The structure is formed the artificial teethridge, the fang and the prosthesis as an integral structure; the thickness of the artificial teethridge is relatively thicker at central part and gradually becomes thinner toward two lateral sides. The structure is specifically a mechanical conduction structure, which can spread and transmit the loading force downwards uniformly;

2. The bottom surface of the artificial teethridge has a complementary structure, which can be tightly matched and fixed on the top surface of the alveolar bone without any gap, whereby the bottom of the artificial teethridge forms a mechanical support structure. Through this complementary arrangement, the loading force which is transmitted from the prosthesis, can be spread and transmitted to each point of the top surface on the alveolar bone completely and uniformly. That is, the "raft foundation" substitutes for the traditional "pile foundation" to load the chewing forces; and 3. The structure of the artificial teethridge, the fang and the prosthesis are specifically an integral structure without any part may be disassembled, which will not cause a fragile structure and a poor force conduction.

All of these three characters of the present invention may be totally or singly designed in a product. Or, single product may also be designed by containing any two of the characters.

Between the prosthesis and artificial teethridge has a dental neck being form in waisted shape, that is narrower at middle section and gradually becomes wider toward to two terminal sections. The artificial teethridge, the dental neck and the prosthesis are an integral structure.

DESCRIPTION OF THE DRAWINGS

The present invention provides an integral structure of the artificial teethridge, the fang and the prosthesis, the scope includes single, partial and full-arched dental fixture. In order to explain the structure, characters and functions of the present invention in detail, we illustrate eight preferred embodiments and the accompanying drawings of full-arched dental fixture in the following description:

FIG. 2-1 is a schematic sectional view of the first preferred embodiment;

DESCRIPTION OF THE EMBODIMENTS

Figure 1:
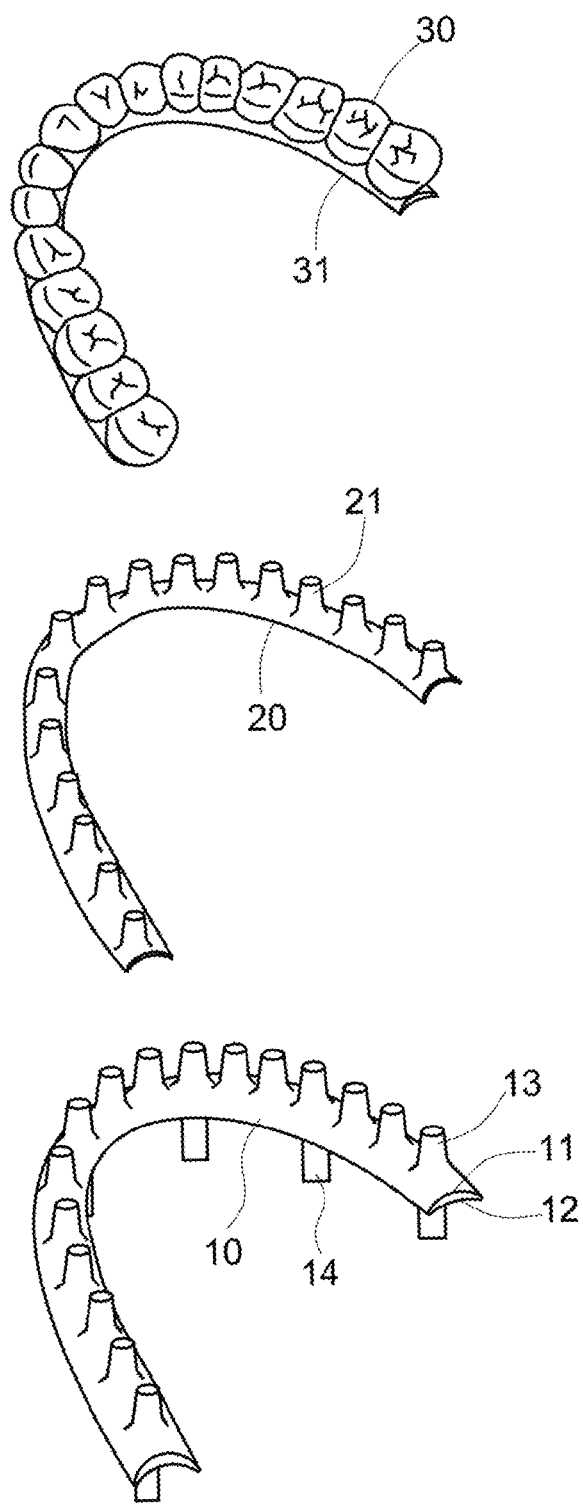
FIG. 1 is an exploded view of the first preferred embodiment.
Figure 2:
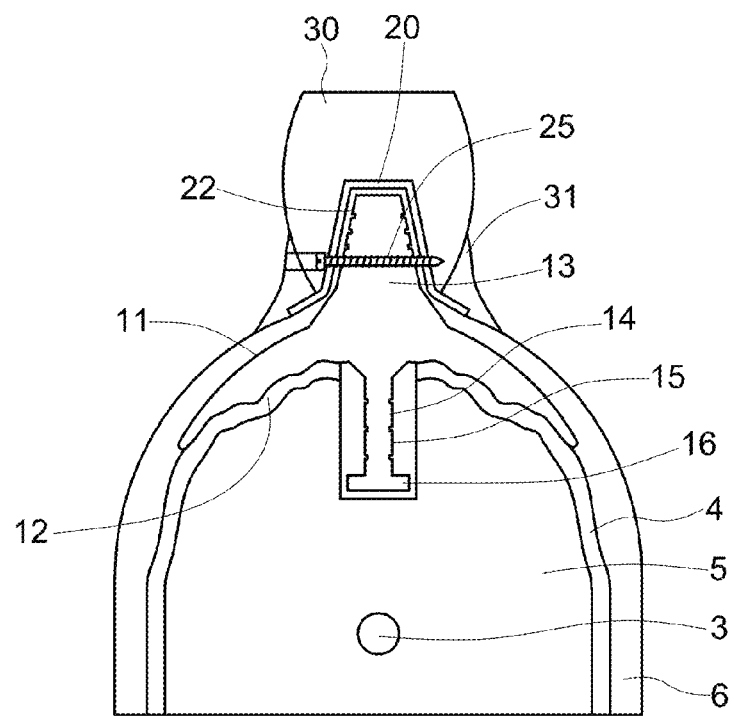
FIG. 2 is a schematic sectional view of the first preferred embodiment.

As shown in FIG. 1 and FIG. 2, the first preferred embodiment of the present invention includes an artificial teethridge 10, a prosthesis base 20 and a prosthesis 30.

The artificial teethridge 10 has a crescent cross-section, which has a shape corresponding to the maxillary or the mandible of human, and the thickness of the artificial teethridge is relatively thicker at central part and gradually becomes thinner toward two lateral sides. The artificial teethridge 10 has an arched top 11 and an arched bottom 12. On the top 11 of the artificial teethridge 10 form integral with the fang 13, and the fang 13 has a narrower fang top and a wider fang bottom. The bottom surface 12 of the artificial teethridge 10 designs a complementary structure which can be tightly matched and fixed on the top of the alveolar bone 5 without any gap, whereby the bottom 12 of the artificial teethridge 10 forms a mechanical support structure. The loading force, which is transmitted from the prosthesis 30, can be spread and transmitted through this structure to each point of the cortical bone 4 uniformly, so the chewing force can be loaded by strong cortical bone 4. Besides, the fastening fixture 14 form integral with the bottom 12 of the artificial teethridge 10.

In the present embodiment, the fastening fixture 14 has lateral flanges 15 on a circumference, and the fastening fixture 14 has an enlarged portion to form a lock portion 16 at the distal end. The lock portion 16 may be replaced by other frictional structure, such as a loop, punctate, or dentate structure, as shown in FIG. 2-1.

The prosthesis base 20, which has an arched shape, can be complementary with the artificial teethridge 10. The prosthesis base 20 has the stake 21 on the base top to mount with the prosthesis 30. The prostheses 30 are connected with each other by an artificial gingival 31 to look natural. The prosthesis base 20 has a cavity 22 corresponding to the fang 13 on the top 11 of the artificial teethridge 10. In practical operation, there is another way to form integral the prosthesis 30 on the fang 13 directly without the prosthesis base 20, and the prosthesis 30, the fang 13, the artificial teethridge 10, the fastening fixture 14 are an integral structure, as shown in FIG. 2-1.

The prosthesis 30, the artificial gingival 31, and the prosthesis base 20 are combined into a denture set, and the denture set is then mounted on the fang 13. There is a gap formed between the bottom of the denture set and the top 11 of the artificial teethridge 10 to receive a gingival 6 therein. If necessary, a screw 25 is fastened to strengthen the conjugation of the denture set and the fang 13, as shown in FIG. 2.

In this embodiment, positioning holes should be preformed on the alveolar bone 5 before the installation of the artificial teethridge 10, and the holes are then filled with biodegradable bone cement or other similar materials, which may be decomposed and replaced by the patient's bone tissue. The lock portions 16 of the fastening fixture 14 is a relatively larger size, thus the fastening fixture 14 will be fixed when the bone cement is cured or replaced by the newly-grown bone tissue. Accordingly, the artificial teethridge 10 will firmly fix to the alveolar bone 5.

Different from the conventional structures which only focus on how to anchor the implant on the impacted cancellous bone, the present invention designs the structure of the artificial teethridge 10 and fang 13 to be mounted and fixed on the surface of the alveolar bone 5. The fang 13 has a narrower fang top and a wider fang bottom, the thickness of the artificial teethridge 10 is relatively thicker at central part and gradually becomes thinner toward two lateral sides. That is, the artificial teethridge 10 and fang 13 form a mechanical conduction structure. Therefore, the chewing force which is transmitted from the prosthesis can be further transmitted downwards and outwards through this structure. The bottom 12 of the artificial teethridge 10, which is designed to be a mechanical support structure and has the function like a so-called "raft foundation" of architecture. The chewing force which is transmitted from the prosthesis is therefore loaded through this structure to entire surface of the cortical bone 4 of the alveolar bone 5 uniformly. It has a great area to load the force uniformly, so that the structure is very strong and has a great capacity to load the chewing force. As a result, the prosthesis 30 can function as well as natural teeth do and can chew the hard food. In addition, due to the alveolar bone 5 having a long-term force loading with a uniform and great area, the alveolar atrophy is impossible.

Even when the patient has a serious alveolar atrophy or osteoporosis, which the alveolar bone 5 has insufficient width, the artificial teethridge 10 and the fang 13 can still be implanted and then mounted with the prosthesis 30 on the fang 13 because the artificial teethridge 10 is mounted and fixed on the strong cortical bone 4 of the alveolar bone 5. Furthermore, the fixing method is to mount the artificial teethridge 10 and the fang 13 on the cortical bone 4, which is different from the prior arts, thus it can reduce the treatment duration. It only takes about a week, instead of six months for the alveolar bone to osseointegrate with the traditional implant, for the gingival 6 to heal up, and then the denture set may be mounted onto the fang 13, accordingly the treatment duration can be significantly shortened.

Figure 3:
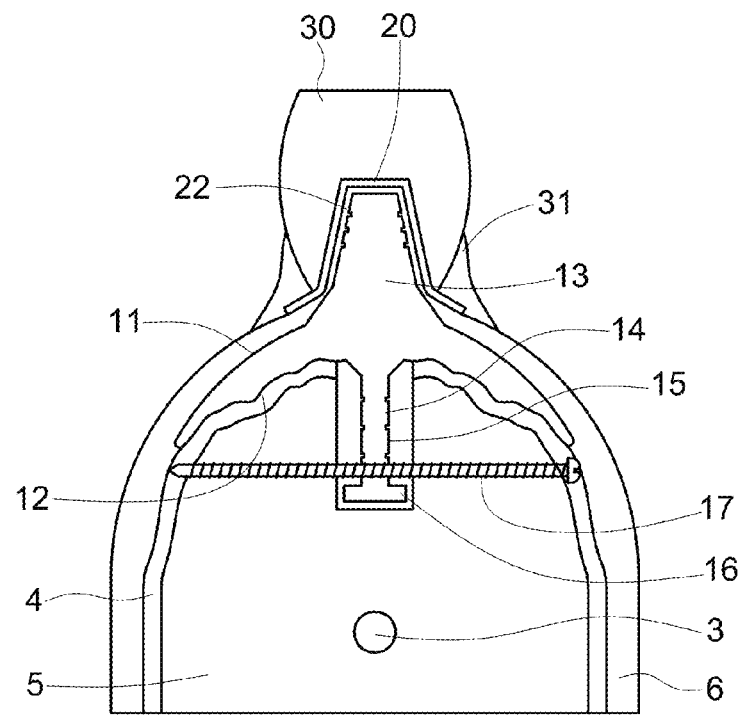
FIG. 3 is a schematic sectional view of the second preferred embodiment.
Figures 1, 2:
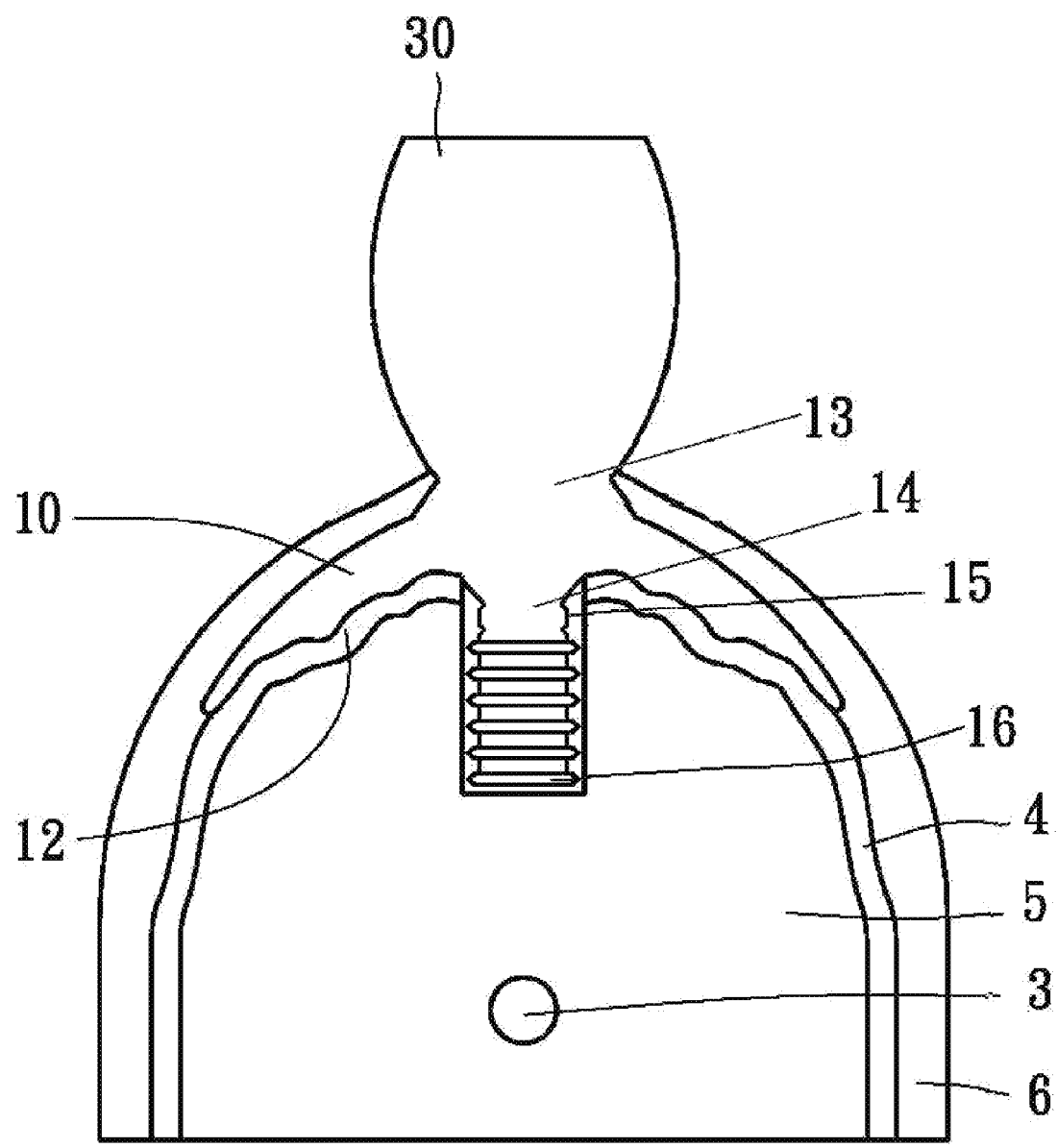

FIG. 3 shows the second preferred embodiment, which the main structure is the same as the first preferred embodiment, except that a transverse screw 17 is set up on the fastening fixture 14 to strengthen the firmness of the artificial teethridge 10 mounted on the alveolar bone 5. It is not necessary to set up the transverse screw 17 on every fastening fixture 14. In practice, it only takes three to five transverse screws 17 for the full dental fixture of the artificial teethridge 10 and fang 13.

Figure 4:
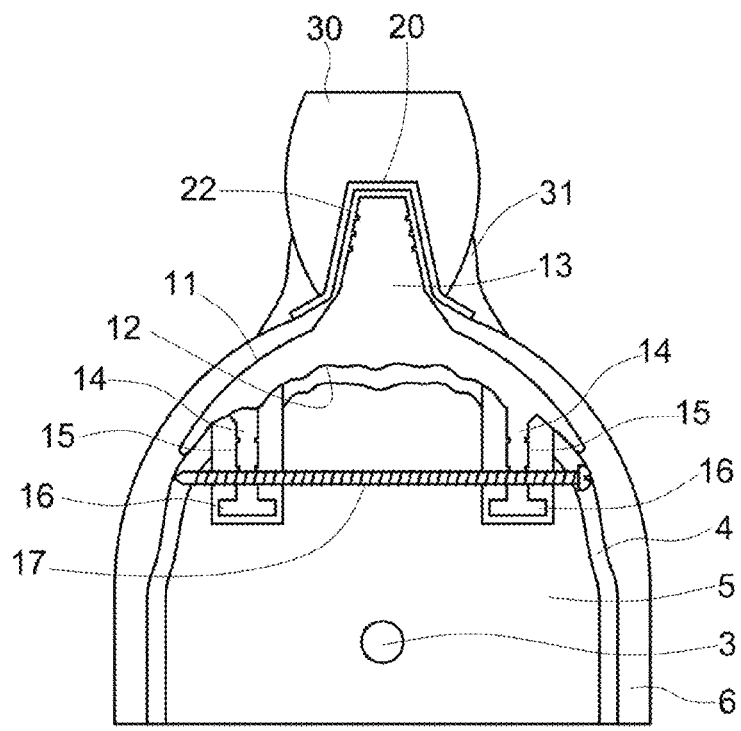
FIG. 4 is a schematic sectional view of the third preferred embodiment.

FIG. 4 shows the third preferred embodiment, which the main structure is similar to the third preferred embodiment, except that a pair of the fastening fixture 14 is set up at the bottom 12 of the artificial teethridge 10, and a transverse screw 17 is fixed between the pair of the fastening fixture 14. It has the same function as the prior preferred embodiment.

Figure 5:
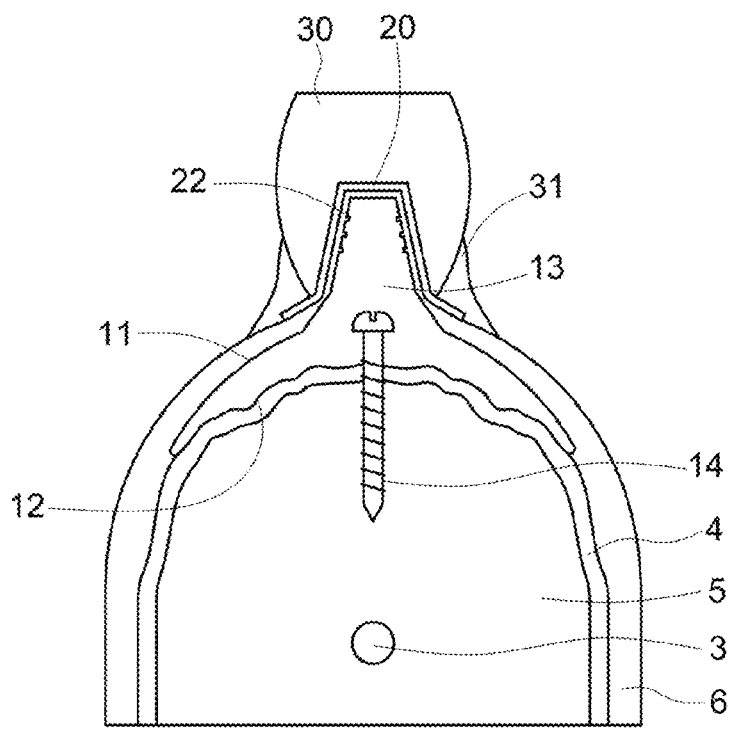
FIG. 5 is a schematic sectional view of the fourth preferred embodiment.

FIG. 5 shows the fourth preferred embodiment, which the main structure is similar to the first preferred embodiment, except that the artificial teethridge 10 has no fastening fixture 14 at the bottom 12, and it replaces the fastening fixture 14 with the fastening screw 14 (screw type of fastening fixture, i.e. fastening screw is another type of fastening fixture) to fix the artificial teethridge 10 on the top of the alveolar bone 5.

Figure 6:
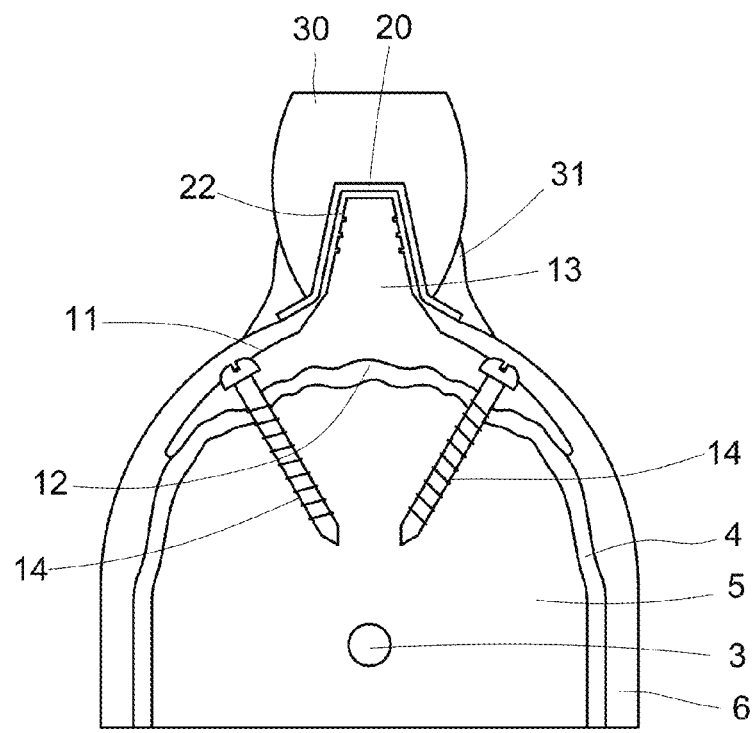
FIG. 6 is a schematic sectional view of the fifth preferred embodiment.

FIG. 6 shows the fifth preferred embodiment, which the main structure is similar to the fourth preferred embodiment and the artificial teethridge 10 is fixed by a pair of fastening screws 14 at two of opposite side to fix the artificial teethridge 10 on the alveolar bone 5.

Figure 7:
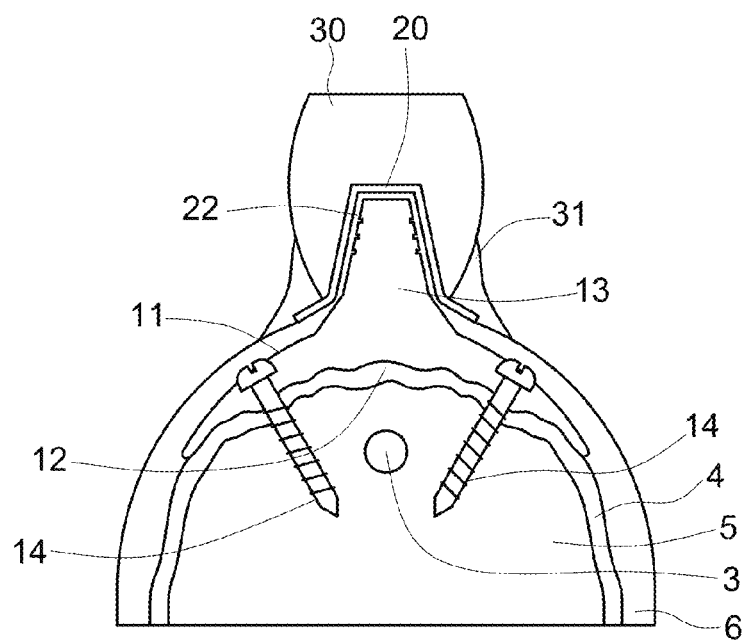
FIG. 7 is another schematic sectional view of the present invention mounted on the alveolar bone.

In the fifth preferred embodiment, the artificial teethridge 10 is directly mounted on the cortical bone 4 of the alveolar bone 5. Therefore, when patient has a serious alveolar atrophy or osteoporosis, which the nerve cavity 3 is too close to the top of the alveolar bone 5 and the width and the height of the alveolar bone 5 are not enough to implant a fixture for mounting the prosthesis, it only has to adjust the width and height of the artificial teethridge 10 depending on the width and the height of patient's alveolar bone 5, thus it is still possible to install this dental fixture without any concern of hurting the nerve 3, as shown in FIG. 7.

Even though there is a little difference between each embodiments as described above, the main structure is the same. All these dental fixtures have a mechanical conduction structure, which has a tapered fang and a crescent carrier, to spread and transmit the chewing force uniformly. And they also have a mechanical support structure, which substitutes the "pile foundation' with the "raft foundation" to load the chewing force, to increase the capacity of force loading. And it also may form the artificial teethridge 10, the fang 13, the fastening fixture 14, and the prosthesis 30 as an integral structure. As a result, the chewing force can be loaded uniformly, and the structure can have a great capacity of force supporting and a firm structure.

Figure 8:
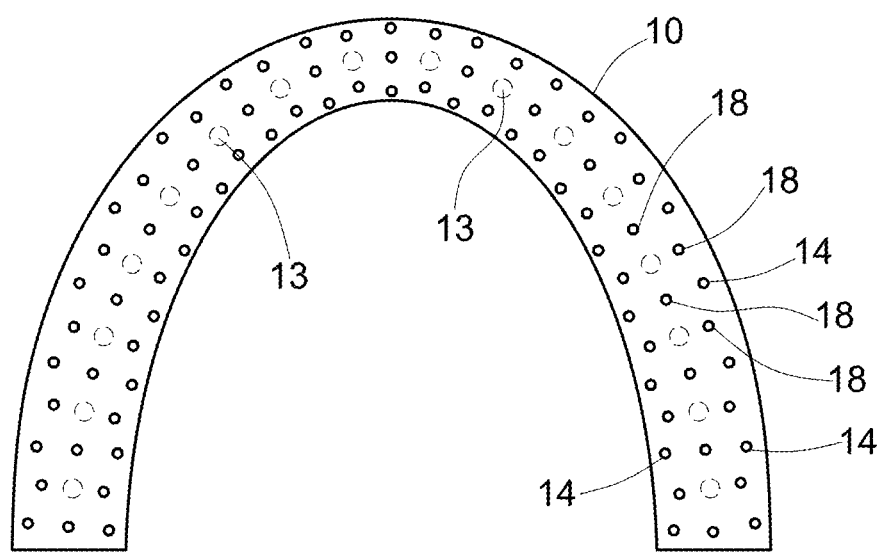
FIG. 8 is a schematic upward view of the artificial teethridge of the sixth preferred embodiment.

Except for the embodiments described in aforesaid, in order to accelerate the gingival 6 to heal over and get completely fixed after mounting the artificial teethridge 10, we design the artificial teethridge 10 with the through holes 18, as shown in FIG. 8, which can promote the integration of the artificial teethridge 10 to human body.

Figure 9:
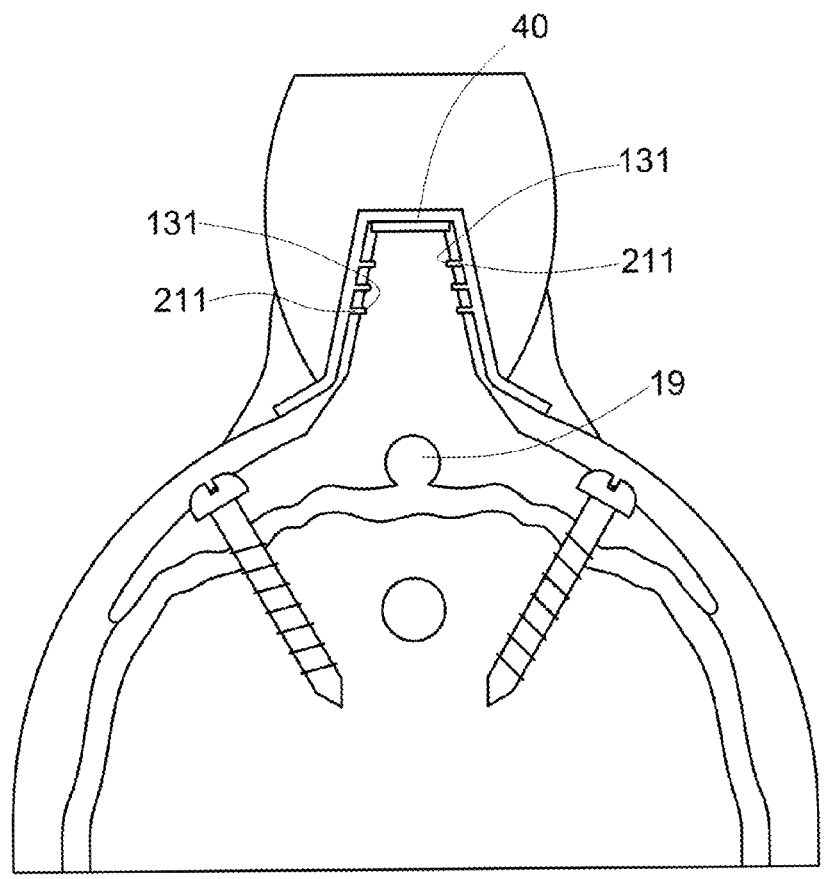
FIG. 9 is a schematic sectional view of the seventh preferred embodiment.

Besides, in order to strengthen the stability of the artificial teethridge 10, the bottom 12 of the artificial teethridge 10 designs a recess 19, which has a narrow opening as shown in FIG. 9, so that the newly-grown bone tissue will enter the recess 19 of the artificial teethridge 10 with a specific technique, which will strengthen the firmness of the artificial teethridge 10. In addition, we design a concave loop 131 around the fang 13 and a corresponding convex loop 211 at the inner wall of the cavity 22 of the prosthesis base 20 to engage with the concave loop 131. Moreover, a cushion pad 40 is fixed on the top of the fang 13 to buffer the chewing force which acts on the denture set to be further transmitted to the fang 13.

Figure 10:
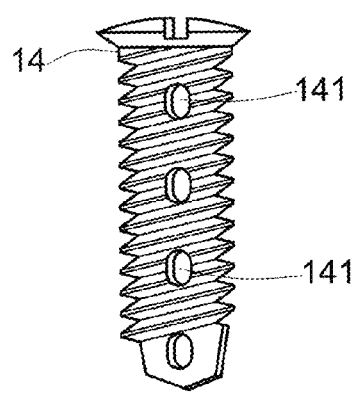
FIG. 10 is a side view of the fastening screw of the fifth and fourth preferred embodiments.

FIG. 10 shows the fastening screw 14 of the fourth, fifth, and seventh preferred embodiments, which could be a regular screw or a round screw with a lock portion 16. The fastening screw 14 has a flat end and multiple through holes 141 on the threaded section and the end. The flat end and the through holes 141 form a lock portion. The function of the fastening screw 14 with the lock portion is to lock the fastening screw 14 on the artificial teethridge 10. Before fixing the fastening screw 14, we will fill the bone-cement in the positioning holes, the cured bone-cement will be decomposed and replaced with the new bone tissue. The new bone tissue may also be generated by osseointegrate without the bone cement. The cured bone-cement or new bone tissue, which is disposed around the flat end and in the through holes 141, will form a lock portion to lock the fastening screw 14 to prevent the fastening screw 14 from being turned and loose.

Figure 11:
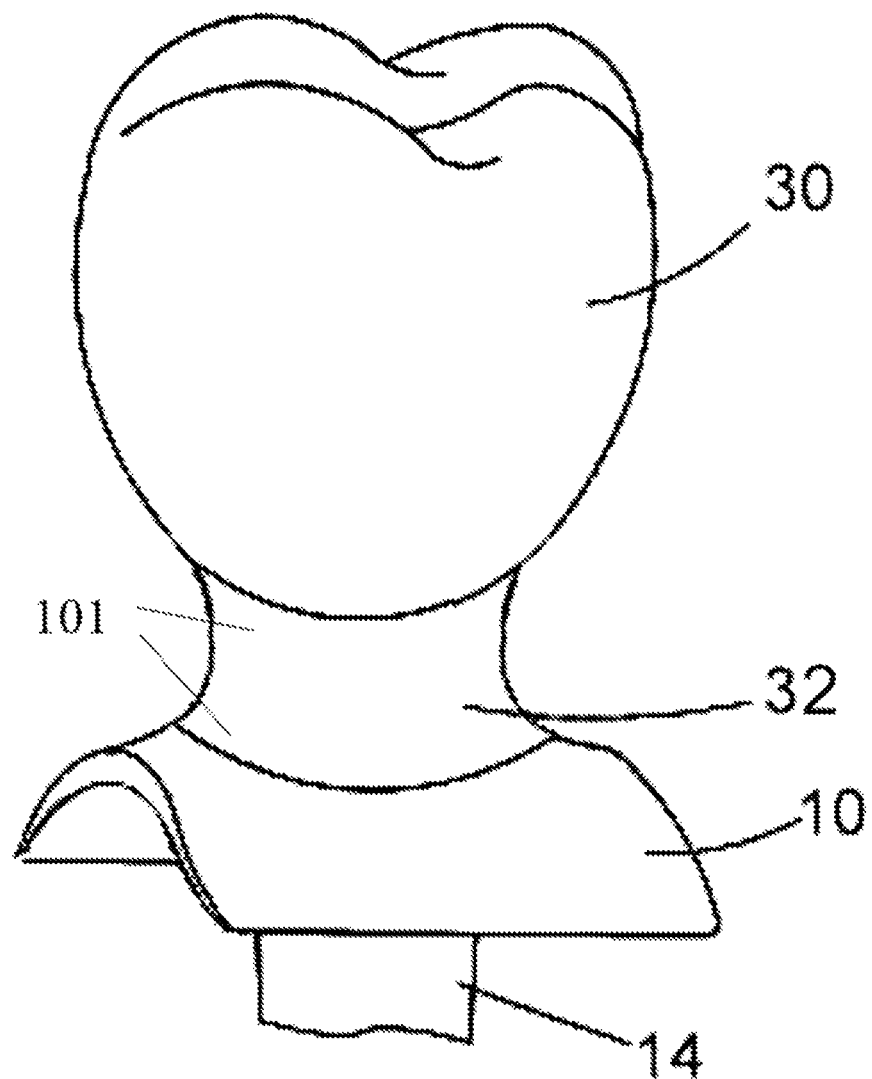
FIG. 11 is a schematic sectional view of the eighth preferred embodiment.

FIG. 11 shows that between the artificial teethridge and prosthesis has a dental neck 32, the artificial teethridge 10, the dental neck 32 and the prosthesis 30 are an integral structure, the dental neck 32 being formed in waisted shape that is narrower at middle section and gradually becomes wider toward to two terminal sections 101. The design of dental neck is for enhancing the attachment effect of gingival connective tissue attach to the surface of the fang, thus further enhancing the biological sealing effect of the cuff, it can prevent further bone loss of the alveolar crest and the vertical reduction of the biological width, it also can prevent the root exposure and aesthetic problems.

Besides these embodiments described above, other embodiments may be made without exceeding the scope of the present invention.

What is claimed is:

1. An artificial teethridge and fang, which is adapted to be mounted and fixed on a top of alveolar bone, comprising:
   a one-piece artificial teethridge, which is formed as a crescent in a cross-sectional view, having an arched top and an arched bottom, the arched top and the arched bottom being arched in the same direction;
   wherein the bottom of the artificial teethridge forms a single concave profile to fit with a curved structure of a top surface of the alveolar bone, so the artificial teethridge is adapted to be mounted and fixed on the alveolar bone;
   a fang integrally formed on the top of the artificial teethridge;
   a prosthesis integrally formed on the top of the fang; and
   a fastening fixture at the bottom of the artificial teethridge;
   wherein the artificial teethridge, the fang, the prosthesis and the fastening fixture are an integral structure;
   between outside of both the artificial teethridge and the prosthesis has a dental neck being formed in a waisted shape, that is narrower at middle section and gradually becomes wider toward to two terminal sections, and a location of the waisted shape is between the two terminal sections viewed along a longitudinal axis of the prosthesis or the fang, to enclose the fang inside the dental neck, and a top terminal section of the two terminal sections is covered on an outer surface of the prosthesis and a bottom terminal section of the two terminal sections is extended from the middle section to stop to cover on a top outer surface of the artificial teethridge; and wherein the artificial teethridge, the dental neck and the prosthesis are an integral structure without any part may be disassembled.

2. The artificial teethridge and fang as defined in claim 1, wherein the thickness of the artificial teethridge is relatively thicker at central part and gradually becomes thinner toward two lateral sides, whereby the artificial teethridge and the fang form a mechanical conduction structure.

3. The artificial teethridge and fang as defined in claim 1, wherein the bottom surface of the artificial teethridge has a complementary structure, which is adapted to be tightly matched and fixed on the top surface of alveolar bone without any gap, whereby the bottom of the artificial teethridge form a mechanical support structure.

4. The artificial teethridge and fang as defined in claim 1, wherein the thickness of the artificial teethridge is relatively thicker at central part and gradually becomes thinner toward two lateral sides, whereby the artificial teethridge forms a mechanical conduction structure, and wherein the bottom surface of the artificial teethridge has a complementary structure, which can be tightly matched and fixed on the curved structure of the top surface of the alveolar bone without any gap, whereby the bottom of the artificial teethridge form a mechanical support structure.

* * * * *